(12) United States Patent
Miller et al.

(10) Patent No.: US 6,919,357 B2
(45) Date of Patent: Jul. 19, 2005

(54) α ADRENERGIC AGENTS

(75) Inventors: Duane D. Miller, Germantown, TN (US); Seoung-Soo Hong, Cheongju (KR)

(73) Assignee: Molecular Design International Inc., Memphis, TN (US)

( * ) Notice: Subject to any disclaimer, the term of this patent is extended or adjusted under 35 U.S.C. 154(b) by 54 days.

(21) Appl. No.: 10/215,547

(22) Filed: Aug. 9, 2002

(65) Prior Publication Data
US 2003/0092741 A1 May 15, 2003

Related U.S. Application Data

(60) Provisional application No. 60/311,320, filed on Aug. 10, 2001.

(51) Int. Cl.[7] .................. A61K 31/4168; C07D 233/88
(52) U.S. Cl. ................. 514/332.5; 548/332.5
(58) Field of Search ...................... 548/332.5; 514/392

(56) References Cited

U.S. PATENT DOCUMENTS 5,731,339 A    3/1998  Lowrey ...................... 514/400

OTHER PUBLICATIONS

J. of Urology vol. 159, 1214–16, 1998; Becker et al.; Oral Pentolamine as Treatment for Erectile Dysfunction.
Int. J. of Impotence Research vol. 6, 37–41, 1994, Zorgniotti, A.W.; Experience with Buccal Phentolamine Mesylate for Impotence.
J. of Sex and Marital Therapy, vol. 25, 137–144, 1999; Rosen et al.; Oral Phentolamine and Female Sexual Arousal Disorder.
Int. J. of Impotence Research, vol. 10, 215–223, 1998; Traish et al.; Phentolamine Mesylate Relaxes Penile Covpus Cavernosum Tissue by Adrenergic and Non–adrenergic Mechanisms.

*Primary Examiner*—Patricia L. Morris

(57) ABSTRACT

Aspects of the present invention are directed towards compounds of Formula I for the treatment of human erectile disorders including erectile dysfunction in men.

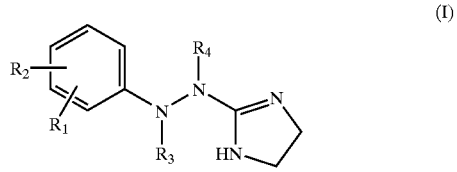

(I)

wherein:

$R_1$ is hydrogen, halo, hydroxy, nitro, cyano, phenyl, trifluoromethyl, $C_1-C_6$ alkyl, $C_1-C_6$ alkoxy, carboxy, amino, cyclohexyl, $C_1-C_6$ alkylamino, or $(C_1-C_6$ alkyl$)_2$ amino;

$R_2$ is hydrogen, halo, hydroxy, nitro, cyano, trifluoromethyl, $C_1-C_6$ alkyl, $C_1-C_6$ alkoxy, carboxy, amino, $C_1-C_6$ alkylamino, or $(C_1-C_6$ alkyl$)_2$amino;

$R_3$ is a group of the formula

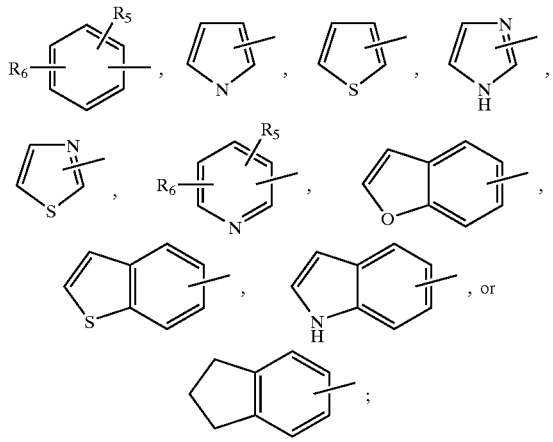

$R_4$ is hydrogen or $C_1-C_6$ alkyl;
$R_5$ is hydrogen, halo, hydroxy, nitro, cyano, phenyl, trifluoromethyl, $C_1-C_6$ alkyl, $C_1-C_6$ alkoxy, carboxy, amino, $C_1-C_6$ alkylamino, or $(C_1-C_6$ alkyl$)_2$amino; and
$R_6$ is hydrogen, halo, hydroxy, nitro, cyano, trifluoromethyl, $C_1-C_6$ alkyl, $C_1-C_6$ alkoxy, carboxy, amino, $C_1-C_6$ alkylamino, or $(C_1-C_6$ alkyl$)_2$amino;

or pharmaceutically acceptable salts thereof.

8 Claims, No Drawings

α ADRENERGIC AGENTS

RELATED APPLICATIONS

This Application claims priority from and benefit of U.S. provision application 60/311,320 filed Aug. 10$^{th}$ 2001.

FIELD OF THE INVENTION

Aspects of the current invention are directed towards the field of organic chemistry and more specifically toward the field of medicinal chemistry.

BACKGROUND OF THE INVENTION

The human sexual response in both males and females results from a complex interplay of psychological, hormonal, and other physiological influences. One important aspect of the human sexual response common to both men and women is the erectile response, which itself results from an interplay between the autonomic nervous system, the endocrine system, and the circulatory system.

Failure of the erectile response, while occurring in both sexes, is most common in men and is referred to as impotence or Erectile Dysfunction (ED). ED is defined as the persistent inability to attain and maintain an erection adequate to permit satisfactory performance. While generally considered a benign disorder, ED has a significant impact on the quality of life experienced by many individuals. It is estimated that 30 million Americans and an additional 46 million men in industrialized countries suffer from some form of ED. The incidence of ED increases with age from about 2 percent at age 40 to about 25% at age 65. In addition, ED is closely associated with certain medical conditions such as cardiovascular disease, hypertension, and diabetes, as well with use of certain prescription medications.

Until recently, medical solutions for ED were invasive, expensive, and often ineffective. These solutions most often included injectable drugs, implants, and pumps. They were met with less than enthusiastic support by patients and obvious drawbacks included pain, risk of infection, inconvenience, and interference with spontaneity. Within the past few years, Pfizer's orally active product Viagra® (sildenafil citrate) has become a break-though treatment for ED. Sildenafil is a potent and selective cGMP-specific type 5 phosphodiesterase inhibitor and now represents the first line therapy for the treatment of ED. Despite sildenafil's success, however, numerous patients have not been successfully treated. In addition, sildenafil must be administered significantly prior to sexual activity ruining spontaneity and numerous side effects have been reported. The most significant side effects relate to visual impairment.

An aspect of the present invention is directed towards novel α receptor antagonists for the treatment of inadequate erectile response. The compounds of the present invention (Formula I) will present another line of therapy for this serious condition in both men and women.

SUMMARY OF THE INVENTION

The present invention provides improved formulations for modulating the human sexual response by administration of a compound of Formula (I) below. Compounds of the present invention are potent antagonists of the alpha receptor family and increase the blood flow to the genitalia and affectuate the improved sexual response. According to the present invention, modulation of the male and female human sexual response is provided on demand by administration of an effective amount of the agent of the present invention. The present invention is directed to improved methods of treating male impotence. Compounds of Formula I include those,

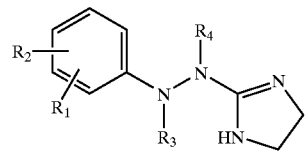

(I)

wherein:

$R_1$ is hydrogen, halo, hydroxy, nitro, cyano, phenyl, trifluoromethyl, $C_1$–$C_6$ alkyl, $C_1$–$C_6$ alkoxy, carboxy, amino, cyclohexyl, $C_1$–$C_6$ alkylamino, or ($C_1$–$C_6$ alkyl)$_2$amino;

$R_2$ is hydrogen, halo, hydroxy, nitro, cyano, trifluoromethyl, $C_1$–$C_6$ alkyl, $C_1$–$C_6$ alkoxy, carboxy, amino, $C_1$–$C_6$ alkylamino, or ($C_1$–$C_6$ alkyl)$_2$amino;

$R_3$ is a group of the formula

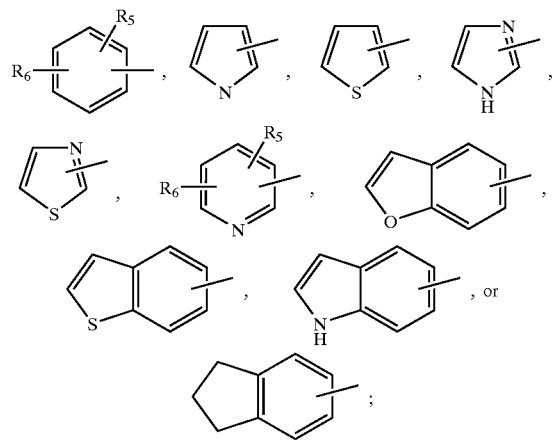

$R_4$ is hydrogen or $C_1$–$C_6$ alkyl;

$R_5$ is hydrogen, halo, hydroxy, nitro, cyano, phenyl, trifluoromethyl, $C_1$–$C_6$ alkyl, $C_1$–$C_6$ alkoxy, carboxy, amino, $C_1$–$C_6$ alkylamino, or ($C_1$–$C_6$ alkyl)$_2$amino; and $R_6$ is hydrogen, halo, hydroxy, nitro, cyano, trifluoromethyl, $C_1$–$C_6$ alkyl, $C_1$–$C_6$ alkoxy, carboxy, amino, $C_1$–$C_6$ alkylamino, or ($C_1$–$C_6$ alkyl)$_2$amino; or pharmaceutically acceptable salts thereof.

The present invention is specifically directed to improved methods of treating male impotence, by administration of a compound of Formula (I) in an amount effective to increase blood flow to the penis. Preferably, the amount of active compound will be effective to improve erectile ability in from about 1 minute to about 60 minutes, more preferably from about 5–15 minutes.

The invention is also specifically directed to methods for modulating the excitation and plateau phases of the female sexual response by administration effective amounts of the compounds of the present invention.

DETAILED DESCRIPTION OF THE INVENTION

The term "$C_1$–$C_6$ alkyl" as used herein includes both straight and branched alkylgroups; including but not limited to methyl, ethyl, propyl, butyl, pentyl, hexyl, isopropyl, sec-butyl, tert-butyl, neopentyl, isopentyl, and the like.

Included within the definition of "$C_1$–$C_6$ alkyl" are also the groups "$C_1$–$C_5$ alkyl", "$C_1$–$C_4$ alkyl", and "$C_1$–$C_3$ alkyl".

The term "alkoxy" as used herein designates an alkyl group attached through an oxygen atom. Examples include but are not intended to be limited to methoxy, ethoxy, pentoxy, and the like.

The term "halo" as used herein includes fluoro, bromo, chloro, and iodo. Preferred halo groups include fluoro and chloro.

The term "modulating sexual response" as used herein means affecting or potentiating the erectile response in men or women. The failure of the erectile response in men to the extent that vaginal penetration and sexual intercourse cannot be achieved is termed "impotence". It is an object of the present invention to increase the strength and or duration of erections in men and to increase arousal and/or engorgement of the genitalia in women. There are striking parallels between the vascular anatomy of men and women and in their associated erectile response. In both males and females, the erectile response takes place when under physical or psychological stimulation, blood flow to the genitalia increases by virtue of relaxation of smooth muscles in the arteries serving the genitalia.

The method of the present invention may be used to improve or enhance the erectile response in women whose sexual response is impaired as evidenced by diminished capacity to produce sufficient vaginal lubrication to facilitate comfortable penile penetration and by other symptoms of impaired sexual responsiveness that may be correlated with the erectile response.

As in the case of male sexual response, in the absence of a clinically diagnosed dysfunction in the female erectile response, the methods of the present invention may be used to enhance the normal female sexual response. The "on demand" aspect of the present invention will allow a more rapid response to sexual stimulation along with heightened sensation associated with excitement and plateau stages of the female sexual response by virtue of the increased blood flow to the genitalia.

The present invention is also useful for affecting the erectile response in other mammals including companion animals such as dogs and cats as well as farm animals such as livestock and horses.

Preferred Embodiments

Preferred compounds of the formula I for use in present invention include compounds wherein:

| $R_1$ is | $R_2$ is |
|---|---|
| a) hydrogen, | a) hydrogen, |
| b) halo, | b) halo, |
| c) phenyl, | c) phenyl, |
| d) amino, | d) amino, |
| e) hydroxy, | e) hydroxy, |
| f) $C_1$–$C_6$ alkyl, or | f) $C_1$–$C_6$ alkyl, or |
| g) $C_1$–$C_6$ alkoxy. | g) $C_1$–$C_6$ alkoxy. |
| $R_5$ is | $R_6$ is |
| a) hydrogen, | a) hydrogen, |
| b) halo, | b) halo, |
| c) phenyl, | c) phenyl, |
| d) amino, | d) amino, |
| e) hydroxy, | e) hydroxy, |
| f) $C_1$–$C_6$ alkyl, or | f) $C_1$–$C_6$ alkyl, or |
| g) $C_1$–$C_6$ alkoxy. | g) $C_1$–$C_6$ alkoxy. |

Especially preferred compound of Formula I are those wherein $R_1$, $R_2$, $R_5$, and $R_6$ are independently selected from the group consisting of hydrogen, $C_1$–$C_6$ alkyl, $C_1$–$C_6$ alkoxy, and halo.

$R_3$ is a)

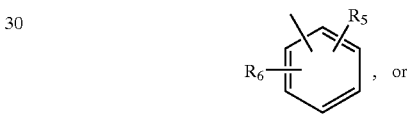

, or b)

.

$R_4$ is
a) hydrogen, or
b) methyl.

Synthetic Methodology

The compounds of Formula I can be prepared according to scheme I below.

Scheme I

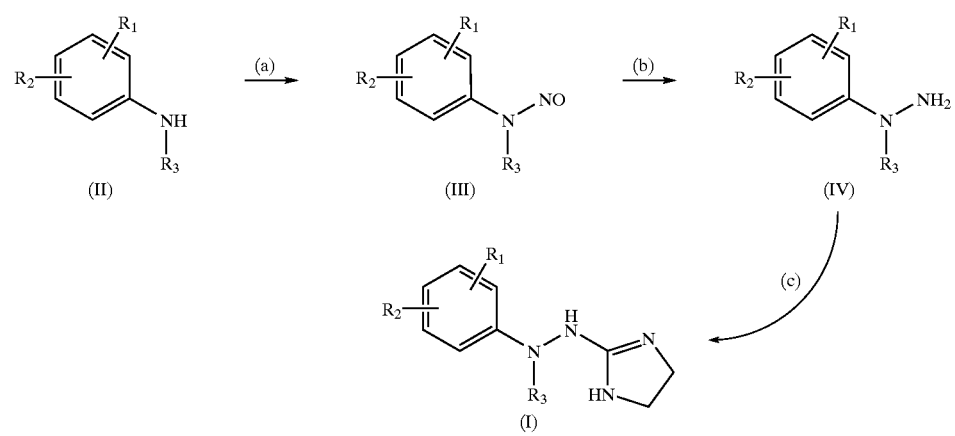

The bis-aryl amines of Formula II are well known in the art, they may be purchased or prepared by methods know and published in the art. For example, they may be prepared by the thermal condensation of an aniline with a phenol. For example, the reaction can be performed at approximately 150–200° C. for about 1 to 48 hours.

The resulting amines of Formula II can be nitrated, in step (a), by procedures well known in the art. They are typically prepared by reacting a compound of Formula II with sodium nitrite in the presence of a mineral acid. Because of the potentially exothermic nature of this reaction, it is typically conducted at subambient temperatures such as 0° C. Since the sodium nitrite is most conveniently added as an aqueous solution, the reaction is typically carried out in a solvent miscible with water such as a lower alcohol, most often ethanol.

The nitrosoamine compounds of Formula III can be reduced, in step (b), to form the hydrazines of Formula IV by standard procedures known to the skilled artisan. Reducing agents such as lithium aluminum hydride (LAH) and the like can be utilized in the reduction. In the case of LAH, the nitrosoamine of Formula III is dissolved in anhydrous diethyl ether and added dropwise to a suspension of LAH. The reaction is typically carried out at room temperature or below and the excess LAH carefully quenched with water while the reaction is being cooled.

The compounds of Formula I can be prepared from the hydrazines of Formula IV, in step (c) by procedures known in the art including but not limited to reacting them with N-acetyl-2-imidazolinone in the presence of $POCl_3$ where the reactants are mixed together and heated to about 100° C. degrees for about 6 hours. Volatile components are then removed under reduced pressure and the resulting reaction products taken up in ethanol, heated to reflux, and then concentrated to yield compounds of Formula I in crude form.

The skilled artisan would appreciate that each of the products from the above reactions could be isolated and purified by techniques known in the art such as extraction by various solvents, crystallization, or chromatography. In addition, the reaction conditions may be varied depending on the solubility, reactivity, and other characteristics of the particular substrates. The skilled artisan will appreciate that elevation of the reaction temperatures will tend to increase the rate of any particular reaction but may often lead to undesired side products. In addition, the substituents $R_1$, $R_2$, and those on $R_3$ may be protected groups as defined herein that need further deprotection to yield final compounds of Formula I. (For example protected hydroxy or protected amino groups). Protection and corresponding deprotection strategies are well known in the art and will vary from specific compound to compound. Protecting groups are chosen based on reaction conditions to be tolerated and specific groups involved. (See Greene supra.)

PREPARATIONS AND EXAMPLES

The following Examples are intended to demonstrate the effectiveness of the present invention. They are not intended to specifically define the variety of conditions under which the present invention can be performed or limit the scope of the claims in any way. A skilled artisan will appreciate, and Applicants assert, that numerous individual alterations of the conditions described herein will also yield effective results.
General:

Except as specifically mentioned, all reactions were conducted, but need not be, under a dry inert atmosphere (argon or nitrogen). All glassware was dried before use in an oven (ca. 150° C.) or flame dried. Solvents and reagents were purified and dried as necessary. Melting points were taken on either a BUCHI 510 melting point apparatus (uncorrected) or an Electrothermal IA9100 digital melting point apparatus. Infrared data were collected on a Perkin-Elmer 783 FTIR spectrophotometer. The NMR spectra were recorded on a BRUKER DPS300 FTNMR spectrometer and reported in parts per million (tetramethylsilane). Data were reported as follows: (s=singlet, d=doublet, t=triplet, q=quartet, m=multiplet, br=broad) integration, interpretation, and coupling constant (Hz). Elemental analyses were obtained from Atlantic Microlab Inc Norcross, Ga., U.S.A. All analytical results for the indicated elements were within 0.4% of the theoretical values. Routine thin-layer chromatography (TLC) was performed on silica gel coated on aluminum plates (silica gel 60 F 254, 20×20 cm, Aldrich Chemical Company Inc Milwaukee, Wis.). Flash column chromatography was performed on silica gel (Merck, grade 60, 230–400 mesh, 60 A).

Preparation 1

3-(4-Methylphenylamino)phenol

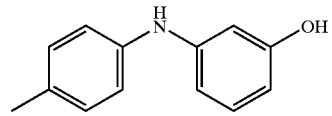

A reaction mixture of p-toluidine (13.4 g, 126.2 mol), resorcinol (10 g, 90.8 mmol) and p-toluidine HCl (1.3 g, 9.0 mmol) was heated at 160° C. for 48 h with an oil bath. After cooling to room temperature, the reaction mixture in 500 mL of diethyl ether was treated with 2N NaOH to give precipitated materials and filtered under reduced pressure. The collected solid was treated with glacial acetic acid until completely dissolved, and the solution was extracted with diethyl ether (2×200 mL). The ether layer was washed with water (2×150 mL), dried over $MgSO_4$, and concentrated under reduced pressure to give a dark-brown oil, which was purified by flash column chromatography using EtOAc/hexane (40:60). The resulting oil was crystallized from $CH_2Cl_2$/hexane to yield 13.4 g (74%) of the title compound as a dark brown solid. Mp 86–88° C. (lit 91° C. )

Preparation 2

3-[(4-Methylphenyl)-N-nitrosoamino]phenol

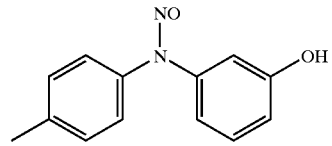

A solution of bis-aryl amine from Preparation 1 (1.0 g, 4.3 mmol) in 6 mL of ethanol was cooled with an ice-water bath and treated with 0.5 mL of concentrated HCl, followed by the addition of a cold solution of $NaNO_2$ (0.33 g, 4.8 mmol) in 0.5 mL of water. After stirring for 1 h, the precipitated material was filtered under reduced pressure to give a solid. The solid was dissolved in 20 mL of $CH_2Cl_2$, and this solution was then washed with 10 mL of water and dried over $MgSO_4$. The solvent was removed under reduced pressure to give a crude solid, which was recrystallized from CH$_2$Cl$_2$/hexane to yield the title compound 0.72 g (73%) as yellow crystals. Mp 113–115° C. (dec). $^1$H NMR (CDCl3/TMS) δ 2.40 (s, 3H, CH3), 6.09 (s, 1H, OH), 6.57–6.63 (m, 1H, ArH), 6.74–6.82 (m, 2H, ArH), 6.91–6.97 (m, 2H, ArH), 7.14–7.33 (m, 3H, ArH).

Preparation 3

N-(3-Methoxyphenyl)-N-(4-methyl phenyl) nitrosoamine

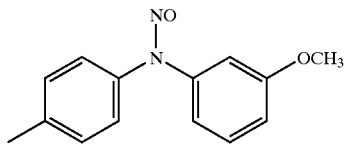

A solution of the compound of Preparation 2 (2.0 g, 9.0 mmol) in 30 ml of acetone was treated with potassium carbonate (2.42 g, 17.5 mmol) and dimethylsulfate (2.21 g, 17.5 mmol). The reaction was heated to reflux for 2.5 h and concentrated under reduced pressure to give a solid. The solid was treated with 30 mL of water, and the mixture was extracted with diethyl ether (2×30 mL). The combined extracts were washed with 30 mL of water, dried over Na$_2$SO$_4$, and concentrated under reduced pressure to yield 1.98 g (91.2%) of the title compound as a yellowish oil: $^1$H NMR (CDCl3/TMS) δ 2.41 (s, 3H, CH3), 3.81 (s, 3H, OCH3), 6.60–6.67 (m, 1H, ArH), 6.83–6.90 (m, 1H, ArH), 6.92–7.00 (m, 2H, ArH), 7.05–7.42 (m, 4H, ArH).

Preparation 4

N-(3-Methoxyphenyl)-N-(4-methyl phenyl) hydrazine hydrochloride

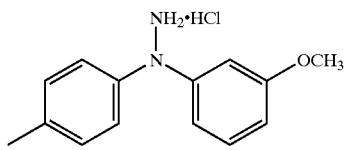

A solution of N-nitrosamine from Preparation 3 (1.79 g 7.39 mmol) in 25 mL of anhydrous diethyl ether was added in a dropwise manner to a suspension of LiAlH$_4$ (0.84 g, 22.2 mmol) in 50 mL of anhydrous diethyl ether. The reaction mixture was stirred at room temperature for 5 h, treated with water while cooling with an ice-water bath to decompose unreacted LiAlH$_4$, filtered, and washed with diethyl ether (3×100 mL). The combined ether solution was washed with 200 mL of water, dried over Na$_2$SO$_4$, and concentrated under reduced pressure to give an oil, which was converted to the HCl salt using excess HCl gas to give 43 g (69.9%) of title compound as off-white crystals: mp 253–255° C. (dec); IR (KBr, cm$^{-1}$) 3856, 3824, 1605; $^1$H NMR (CD3OD) δ 2.37 (s, 3H, CH3), 3.76(s, 3H, OCH3), 6.58–6.6 (m, 2H, ArH), 6.77–6.80 (m, 1H, ArH), 7.13–7.16 (m, 2H, ArH), 7.27–7.33 (m, 3H, ArH).

Example 1

2-[2-(3-Methoxyphenyl)-2-(4-methyl phenyl) hydrazino] imidazoline oxalate

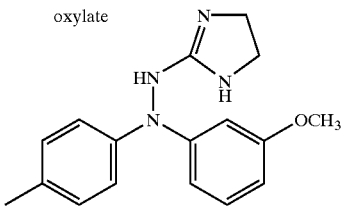

Mixture of hydrazine hydrochloride from Preparation 4 (0.7 9, 2.5 mmol) and N-acetyl-2 imidazolinone (0.65 g, 5.1 mmol) in 10 mL of POCl$_3$ was heated to 100° C. in an oil bath for 6 h. The excess POCl$_3$ was removed under reduced pressure to give a dark brown oil, which was taken up in 50 mL of EtOH and heated to reflux for 1 h. The mixture was concentrated under reduced pressure to give an oil which was treated with 30 mL of a saturated sodium bicarbonate solution and extracted with CH$_2$Cl$_2$ (3×25 mL). The combined extracts were washed with 30 mL of water, dried over Na$_2$SO$_4$, and concentrated under reduced pressure to give an oil, which was purified by flash column chromatography using a gradient CH$_2$Cl$_2$ to CH$_2$Cl$_2$/MeOH (90:10). The obtained solid was recrystallized from MeOH/Et$_2$O to give 0.52 g (69%) of the free base as colorless crystals. Treating with oxalic acid in diethyl ether provided the oxalate salt: mp 178–180° C.; IR (KBr, cm1) 3437, 1647, 1592; $^1$H NMR (CDCl3/TMS) δ 2.30 (5, 3H, CH3), 3.47 (5, 4H, 2×CH2), 3.74 (5, 3H, OCH3), 6.42–6.46 (m, 1H, ArH), 6.60–6.66 (m, 2H, ArH), 7.07–7.14 (m, 5H ArH).

Example 2

2-[2-(3-Hydroxyphenyl)-2-(4-methyl phenyl) hydrazine] imidazoline hydrochloride

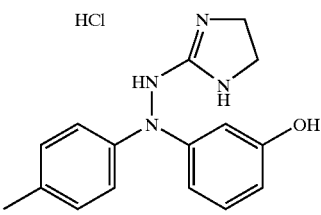

Oxalate salt from Example 1 was converted to the free base. A solution of free base (0.5 g, 1.7 mmol) in 50 mL of anhydrous CH$_2$Cl$_2$ under a dry ice-acetone bath was treated in a dropwise manner with 5.1 mL of BBr$_3$ (1 M solution in CH$_2$Cl$_2$, 5.1 mmol) under an argon atmosphere. The reaction mixture was warmed gradually to room temperature and stirred for 15 h, and then treated with MeOH while cooling with an ice water bath. The resulting mixture was concentrated under reduced pressure to give an oil (3×30 mL), which was treated with 50 mL of sat. NaHCO$_3$ solution. The mixture was extracted with CH$_2$Cl$_2$ (2×50 mL), and the extracts were washed with water (2×50 mL), dried over MgSO$_4$, concentrated under reduced pressure, and purified by flash column chromatography using CH$_2$Cl$_2$/MeOH (90–10) to give an oil. This product was converted to the HCl salt using excess 1 N HCl solution in diethyl ether, and crystallized from MeOH/Et$_2$0 to give 0.38 g (62%) of the title compound as a brown solid: mp 247–250° C. (dec); IR (KBr, cm-1) 2985, 1985, 1789; $^1$H NMR (CD3OD) δ 2.33 (5, 3H, CH3), 3.74 (br5, 4H, 2×CH2), 6.43–6.52 (m, 3H, ArH), 7.08–7.13 (m, 3H, ArH), 7.14–7.22 (m, 2H, ArH).

The following Examples were, or could be prepared substantially in accordance with the Preparations and Examples listed above.

Example 3

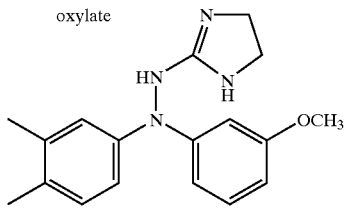

The compound of Example 3 was prepared from 3-(3,4-dimethylphenylamino)phenol substantially in accordance with the procedures of Preparations 2–4 and Example 1. Product MW as confirmed to be 400.43.

Example 4

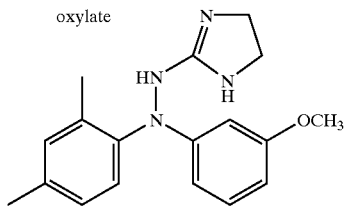

The compound of Example 4 was prepared from 3-(2,4-dimethylphenylamino)phenol substantially in accordance with the procedures of Preparations 2–4 and Example 1. Product MW as confirmed to be 411.24 (0.6 H2O).

Example 5

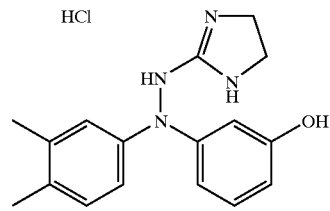

The compound of Example 5 can be prepared from the product of Example 3 substantially in accordance with procedures of Example 2.

Example 6

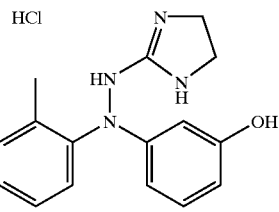

The compound of Example 6 was prepared from the product of Example 4 substantially in accordance with the procedures of Example 2. Product MW as confirmed to be 333.83.

Example 7

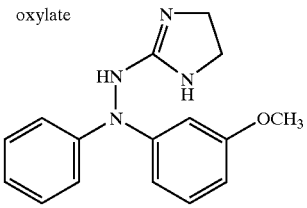

The compound of Example 7 was prepared from 3-phenylaminophenol substantially in accordance with the procedures of Preparations 2–4 and Example 1. Product MW as confirmed to be 347.17 (0.6 oxylate 0.6 H2O).

Example 8

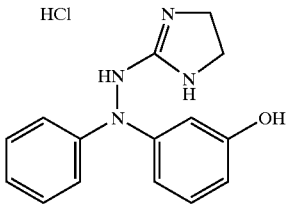

The compound of Example 8 can be prepared from the product of Example 7 substantially in accordance with the procedures of Example 2

Example 9

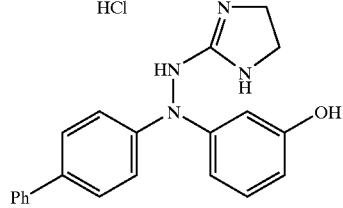

The compound of Example 4 can be prepared from 3-(p-biphenylamino)phenol substantially in accordance with the procedures of Preparations 2–4 and Examples 1 and 2.

Example 10

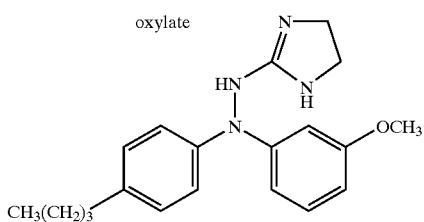

The compound of Example 10 was prepared from 3-(4-n-butylphenylamino)phenol substantially in accordance with the procedures of Preparations 2–4 and Example 1. Product MW as confirmed to be 390.66 (0.4 oxylate 0.9 H2O).

Example 11

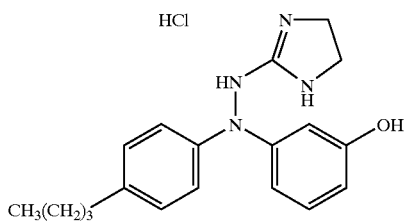

The compound of Example 11 was prepared from the product of Example 10 substantially in accordance with the procedures of Example 2. Product MW as confirmed to be 360.88.

Example 12

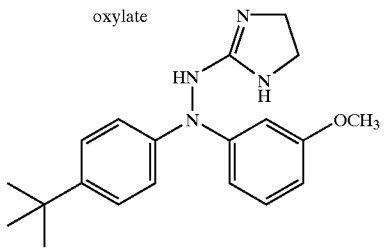

The compound of example 12 was prepared from 3-(4-t-butylphenylamino)phenol substantially in accordance with the procedures of preparations 2–4 and example 1. Product MW as confirmed to be 394.26 (0.4 oxylate 1.1 H2O).

Example 13

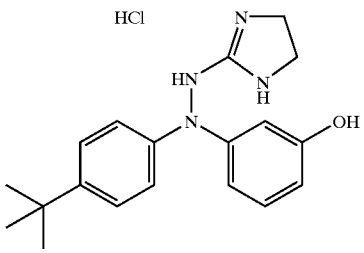

The compound of Example 13 was prepared from the product of Example 12 substantially in accordance with the procedures of Example 2. Product MW as confirmed to be 366.27 (0.3 H2O).

Example 14

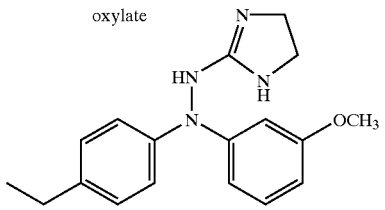

The compound of Example 14 was prepared from 3-(4-ethylphenylamino)phenol substantially in accordance with the procedures of Preparations 2–4 and Example 1. Product MW as confirmed to be 400.43.

Example 15

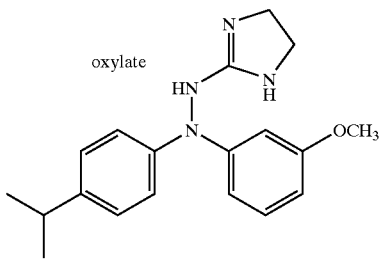

The compound of Example 15 was prepared from 3-(4-isopropylphenylamino)phenol substantially in accordance with the procedures of Preparations 2–4 and Example 1. Product MW as confirmed to be 373.04 (0.4 oxylate 0.7 H2O).

Example 16

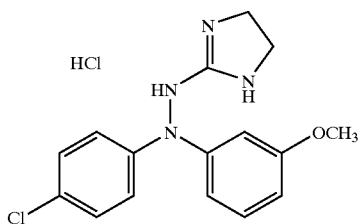

The compound of Example 16 was prepared from 3-(4-chlorophenylamino)phenol substantially in accordance with the procedures of Preparations 2–4 and Example 1. Product MW as confirmed to be 365.85 (0.7 H2O).

Example 17

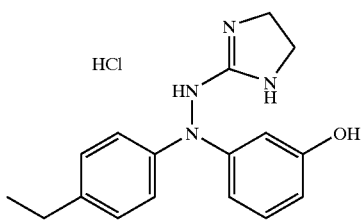

The compound of Example 17 can be prepared from the product of Example 14 by the procedure of Example 2.

Example 18

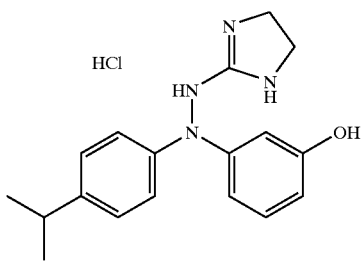

The compound of Example 18 can be prepared from the product of Example 15 by the procedure of Example 2.

Example 19

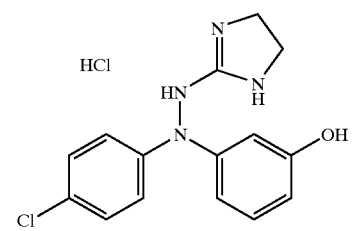

The compound of Example 19 was prepared from the product of Example 16 by the procedure of Example 2. MW was confirmed to be 339.22.

Example 20

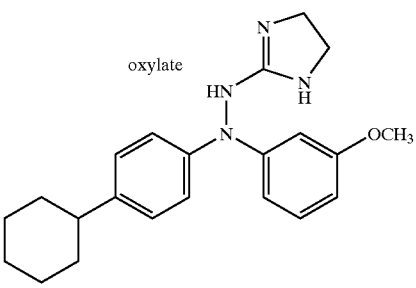

The compound of Example 20 was prepared from 3-(4-cyclohexylphenylamino)phenol substantially in accordance with the procedures of Preparations 2–4 and Example 1. Product MW as confirmed to be 454.52.

Example 21

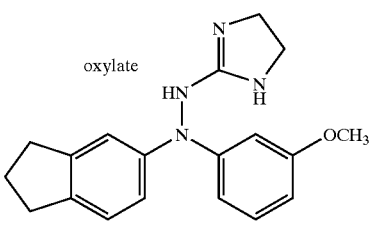

The compound of Example 21 was prepared from 5-(2,3-dishydroindenylphenylamino)phenol substantially in accordance with the procedures of Preparations 2–4 and Example 1. Product MW as confirmed to be 412.44.

Example 22

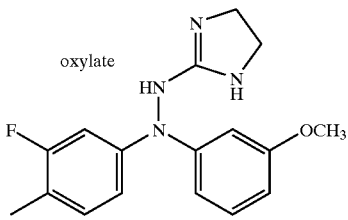

The compound of Example 22 can be prepared from 3-(3-fluoro-4-methylphenylamino)phenol substantially in accordance with the procedures of Preparations 2–4 and Example 1. Product MW as confirmed to be 394.26 (0.4 oxylate 1.1 H2O).

Biological Results and Discussion

Compounds of the present invention can be functionally tested for α-adrenergic activity on rat aorta, and binding affinities for human α-2a-adrenergic receptors can be assessed. All compounds of the present invention blocked phenylephrine-induced contractions of rat aorta, and produced parallel shifts in the dose-response curve of the α-adrenoceptor agonist phenylephrine. As compared to phentolamine ($K_b$, 11.8 nM), Example 2 was 4.1 times more potent an antagonist of the vascular response ($K_b$, 2.9 nM). Methoxy analog from Example 1 (7.4 nM) was also more potent than phentolamine.

Using [3H]rauwolscine as the radioligand, the binding affinities of compounds of the present invention were determined with Chinese hamster ovary (CHO) cells expressing human α2a adrenoceptors.

Pharmacology

Rat Aorta Assay.

Male albino rats (300–350 g) were used to obtain thoracic aorta after exposure to dry ice. Aortic strips were suspended in 10 mL organ baths containing physiological salt solutions maintained at 37° C. and continuously bubbled with a 5% $CO_2$—95% $O_2$ mixture. Aortic strips were preincubated for 60 min with the compound to be tested ($10^{-8}$ M) before construction of the concentration-response curve for each drug. Matched control strips without the blocking drug were used and the shifts in the concentration-response curve were analyzed for the determination of the dissociation constant $K_b$ value for the antagonist. A maximal was adjusted from this value.

Competitive Equilibrium Binding Assay.

The binding of [3H]rauwolscine (0.1 $\mu$Ci, 5 nM) to human α2a-adrenoceptor subtype can be conducted at room temperature in a final volume of 2 ml. Nonspecific binding of radioligand can be defined by addition of 10 $\mu$M yohimbine, and specific binding was usually equal to 98–100% of total binding. Inhibition of specific binding of the competitors can be determined using varying concentrations compounds. After 60 minutes of incubation, samples can be rapidly filtered by vacuum through Whatman GF/C fiber filters on a Brandel cell harvester (Model M 12-RI), and washed three times with 5 ml Tris-EDTA buffer (in mM: Trisma base, 23; Trisma HCl, 27; NaCl 154; EDTA, 20; ascorbic acid, 1 pH 7.4) The filter disks can be submerged in 3 ml of scintillation cocktail (Ultima Gold XR, Packard Instrument Company) in plastic vials, vortexed, and [3H] measured by liquid scintillation spectrometry (LKB Wallac Liquid Scintillation, Model 1219 Rackbeta). Percent specific binding can be calculated as (total binding−nonspecific binding)/total binding×100%. IC50 values for each drug can be determined using GraphPad Prism. All data should represent the mean of 4–6 experiments While it is possible to administer a compound employed in the methods of the present invention directly without any formulation, the compounds are usually administered in the form of a pharmaceutical composition comprising a pharmaceutically acceptable excipient and at least one active ingredient. The compositions can be administered by a variety of routes including oral, rectal, transdermal, subcutaneous, intravenous, intramuscular, intranasel, and intercavernosal. Many of the compounds employed in the methods of this invention are effective as both injectable and as oral compositions. Such compositions are prepared in a manner well known in the pharmaceutical art and comprise at least one active compound. See, e.g., REMINGTON'S PHARMACEUTICAL SCIENCES, (16$^{th}$ ed. 1980).

The compositions are generally formulated in a unit dosage form, each dosage containing from about 0.05 to about 100 mg, more usually about 1.0 to about 30 mg, of the active ingredient. The term "unit dosage form", refers to physically discrete units suitable as unitary dosages for human subjects and other mammals, each unit containing a predetermined quantity of active material calculated to produce the desired therapeutic effect, in association with a suitable pharmaceutical excipient. Appropriate doses of each vasoactive agent for compounds of the present invention for each route of administration are readily determined by those of ordinary skill in the art. By way of illustration, in order to determine the appropriate does of each of the agents of the present invention, one of ordinary skill in the art may use as a starting point, the usual published dose of related vasodilators. Such doses are published in the Physician Desk Reference published annually by Medical Economic Data, Montvale N.J. and in other available medical literature.

The active compounds are generally effect over a wide dose range. For example, dosages per day normally fall within the range of about 0.01 to about 30 mg/kg of body weight. In the treatment of adult humans, the range of about 0.1 to about 15 mg/kg, in a single or divided dose, is especially preferred. A skilled artisan would understand, however, that the amount of compound actually administered will be determined by a physician, in light of the relevant circumstances, including the condition to be treated, the chosen route of administration, as well as the age, weight, and individual patient symptoms. Larger or smaller doses may be appropriate in the discretion of the physician.

Formulation Example 1

Hard gelatin capsules containing the following ingredients are prepared by mixing the ingredients an filling them into hare gelatin capsules in 340 mg quantities:

| | |
|---|---|
| Compound of Example 1 | 30 mg |
| Starch | 305 mg |
| Magnesium Stearate | 5 mg |

Formulation Example 2

A tablet containing the following ingredients are prepared by mixing the ingredients and compressing them to form tablets, each weighing 240 mg.

| | |
|---|---|
| Compound of Example 2 | 25 mg |
| Cellulose, microcrystalline | 200 mg |
| Colloidal silicon dioxide | 10 mg |
| Stearic acid | 5 mg |

We claim:

1. A compound of Formula I

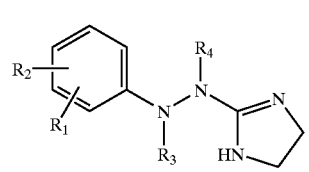

(I)

wherein:

$R_1$ is hydrogen, halo, hydroxy, nitro, cyano, phenyl, trifluoromethyl, $C_1$–$C_6$ alkyl, $C_1$–$C_6$ alkoxy, carboxy, amino, cyclohexyl, $C_1$–$C_6$ alkylamino, or ($C_1$–$C_6$ alkyl)$_2$amino;

$R_2$ is hydrogen, halo, hydroxy, nitro, cyano, trifluoromethyl, $C_1$–$C_6$ alkyl, $C_1$–$C_6$ alkoxy, carboxy, amino, $C_1$–$C_6$ alkylamino, or ($C_1$–$C_6$ alkyl)$_2$amino;

$R_3$ is a group of the formula

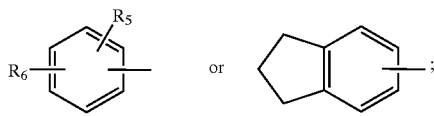

$R_4$ is hydrogen or $C_1$–$C_6$ alkyl;

$R_5$ is hydrogen, halo, hydroxy, nitro, cyano, phenyl, trifluoromethyl, $C_1$–$C_6$ alkyl, $C_1$–$C_6$ alkoxy, carboxy, amino, $C_1$–$C_6$ alkylamino, or ($C_1$–$C_6$ alkyl)$_2$amino; and $R_6$ is hydrogen, halo, hydroxy, nitro, cyano, trifluoromethyl, $C_1$–$C_6$ alkyl, $C_1$–$C_6$ alkoxy, carboxy, amino, $C_1$–$C_6$ alkylamino, or ($C_1$–$C_6$ alkyl)$_2$amino;

or a pharmaceutically acceptable salt thereof.

2. A compound of claim 1 wherein: $R_3$ is a group of the formula

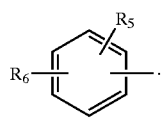

3. A compound of claim 2 wherein:

$R_1$ is hydrogen, halo, hydroxy, $C_1$–$C_6$ alkyl, $C_1$–$C_6$ alkoxy, amino, cyclohexyl, $C_1$–$C_6$ alkylamino, or ($C_1$–$C_6$ alkyl)$_2$amino; and $R_2$ is hydrogen, halo, hydroxy, $C_1$–$C_6$ alkyl, $C_1$–$C_6$ alkoxy, amino, $C_1$–$C_6$ alkylamino, or ($C_1$–$C_6$ alkyl)$_2$amino.

4. A compound of claim 3 wherein:

$R_5$ is hydrogen, halo, hydroxy, $C_1$–$C_6$ alkyl, $C_1$–$C_6$ alkoxy, amino, cyclohexyl, $C_1$–$C_6$ alkylamino, or ($C_1$–$C_6$ alkyl)$_2$amino; and $R_6$ is hydrogen, halo, hydroxy, $C_1$–$C_6$ alkyl, $C_1$–$C_6$ alkoxy, amino, $C_1$–$C_6$ alkylamino, or ($C_1$–$C_6$ alkyl)$_2$amino.

5. A compound of claim 4 wherein $R_4$ is hydrogen.

6. A compound of claim 5 wherein:

$R_1$ is hydrogen, halo, hydroxy, $C_1$–$C_6$ alkyl, or $C_1$–$C_6$ alkoxy;

$R_2$ is hydrogen, halo, hydroxy, $C_1$–$C_6$ alkyl, or $C_1$–$C_6$ alkoxy;

$R_5$ is hydrogen, halo, hydroxy, $C_1$–$C_6$ alkyl, or $C_1$–$C_6$ alkoxy; and $R_6$ is hydrogen, halo, hydroxy, $C_1$–$C_6$ alkyl, or $C_1$–$C_6$ alkoxy.

7. A pharmaceutical formulation comprising as an active ingredient a compound of claim 1 associated with one or more pharmaceutically acceptable carriers, excipients, or diluents.

8. A pharmaceutical formulation comprising as an active ingredient a compound of claim 6 associated with one or more pharmaceutically acceptable carriers, excipients, or diluents.

* * * * *